(12) United States Patent
Carley

(10) Patent No.: US 10,245,134 B2
(45) Date of Patent: Apr. 2, 2019

(54) APPARATUS AND METHODS FOR THE TREATMENT OF URINARY INCONTINENCE

(71) Applicant: Michael E. Carley, Dallas, TX (US)

(72) Inventor: Michael E. Carley, Dallas, TX (US)

( * ) Notice: Subject to any disclaimer, the term of this patent is extended or adjusted under 35 U.S.C. 154(b) by 115 days.

(21) Appl. No.: 14/622,848

(22) Filed: Feb. 14, 2015

(65) Prior Publication Data

US 2015/0230905 A1    Aug. 20, 2015

Related U.S. Application Data

(60) Provisional application No. 61/940,467, filed on Feb. 16, 2014.

(51) Int. Cl.
*A61F 2/00* (2006.01)

(52) U.S. Cl.
CPC .... *A61F 2/0045* (2013.01); *A61F 2210/0004* (2013.01); *A61F 2210/0071* (2013.01); *A61F 2220/0016* (2013.01); *A61F 2250/0031* (2013.01); *A61F 2250/0078* (2013.01)

(58) Field of Classification Search
CPC ................ A61F 2/0045; A61F 2/0063; A61F 2002/068; A61B 2017/00805
See application file for complete search history.

(56) References Cited

U.S. PATENT DOCUMENTS

| | | | |
|---|---|---|---|
| 2002/0028980 A1* | 3/2002 | Thierfelder | A61B 17/00234 600/37 |
| 2002/0038151 A1* | 3/2002 | Plouhar | A61F 2/0063 623/23.72 |
| 2003/0023316 A1* | 1/2003 | Brown | A61F 2/0063 623/23.72 |
| 2004/0144395 A1* | 7/2004 | Evans | A61B 17/06066 128/885 |
| 2006/0195010 A1* | 8/2006 | Arnal | A61B 17/06066 600/30 |
| 2008/0004490 A1* | 1/2008 | Bosley, Jr. | A61B 17/06109 600/37 |
| 2011/0184441 A1* | 7/2011 | St-Germain | A61F 2/0063 606/151 |
| 2013/0012768 A1* | 1/2013 | Koullick | A61L 31/06 600/37 |
| 2013/0116799 A1* | 5/2013 | Derwin | A61F 2/02 623/23.72 |
| 2015/0094525 A1* | 4/2015 | Tomc | A61B 17/06109 600/37 |

* cited by examiner

*Primary Examiner* — Thaddeus B Cox
(74) *Attorney, Agent, or Firm* — The Courtney Firm; Mark Courtney

(57) ABSTRACT

Devices and methods for treating urinary incontinence are disclosed. In one embodiment, an implantable device uses non-biodegradable suture(s) positioned under or adjacent to the urethra. The sutures may be anchored by one of several methods including integration with mesh, tines, barbs, or an alternative anchoring system away from the urethra. A delivery system may comprise a hollow trocar with removable tip and handle. Methods for treating urinary incontinence using the devices are disclosed.

20 Claims, 6 Drawing Sheets

APPARATUS AND METHODS FOR THE TREATMENT OF URINARY INCONTINENCE

RELATED APPLICATIONS

This patent application claims priority to U.S. Provisional Patent Application Ser. No. 61/940,467, entitled "URETHRAL SUTURE SLING AND IMPLANTATION DEVICES AND SYSTEMS FOR THE TREATMENT OF URINARY INCONTINENCE," filed on Feb. 16, 2014, which application is hereby incorporated by reference herein in its entirety.

TECHNICAL FIELD

This application relates to the field of surgical treatment of urinary incontinence. More specifically, the various embodiments are directed to sling implant(s) formed using sutures placed underneath or adjacent to the urethra. In various embodiments, non-biodegradable mesh or an anchoring system are positioned away from the urethra, the anchors are configured to minimize movement of the sutures.

BACKGROUND

In the United States, one in four women over forty years of age suffer from some form of urinary incontinence. Normal urination occurs from the coordinated contraction of the bladder or detrusor muscle and with the simultaneous relaxation of the urethra or sphincter muscle. Urinary incontinence occurs as a consequence of either an unwanted contraction of the bladder muscle leading to urge incontinence, or from poor urethral or sphincter tone leading to urinary incontinence during times of physical exertion on the bladder.

Many women suffer from stress urinary incontinence. Stress urinary incontinence is defined by the International Continence Society as "the involuntary leakage of urine during increased abdominal pressure, in the absence of a detrusor contraction." This form of urinary incontinence most often occurs with activities such as exercise, coughing, laughing, and sexual activity. Urinary incontinence has been associated with childbirth, aging, declining estrogen levels, and genetic predisposition. Urinary incontinence has an unfortunate negative impact on the patient's quality of life. Given its profound impact, many women seek medical treatment for this condition. Treatment of stress unitary incontinence is broadly aimed at improving the function of the urethra to aid in its closing during times of physical stress.

In the prior known approaches, treatment of stress urinary incontinence has included the use of non-surgical modalities such as pelvic floor physical therapy and the use of pessaries. Pelvic floor physical therapy is used to strengthen the muscles of the pelvic floor, a component of these muscles include those that encircle the urethra. Pessaries are mechanical devices placed within the vagina and which exert pressure on the urethra. In-office surgical procedures have included the use of bulking agents that can be injected into the urethra to aid in closure and to increase resistance and the use of transurethral radiofrequency to cause collagen remodeling to aid in urethral closure. In other approaches, surgical procedures which require operating room procedures have included retropubic procedures that support the urethra from a transabdominal approach and autologous sling procedures using harvested tissue.

The morbidity of these prior known approaches led to development of urethral sling procedures. In a typical sling procedure, a sling device is placed vaginally with minimal incisions. Transvaginal sling procedures using cadaver tissue or heterologous tissue have been used. These slings have had high failure rates. These high failure rates are likely due to tissue degradation. Suburethral synthetic sling procedures have been developed. In these procedures synthetic mesh sling material is placed proximal to the urethra and beneath it, to provide a suburethral sling. Unfortunately, procedures using suburethral synthetic mesh are frequently associated with complications. These complications include erosion of the synthetic mesh, pain secondary to collagen integration into the mesh with scar plate formation and contraction, and difficulty in mesh removal should erosion occur.

The development of synthetic slings has been a great advancement in the treatment of urinary incontinence in women. However, current designs for the implant utilize synthetic mesh. The synthetic mesh is implanted suburethrally. These designs have high success rates in reducing incontinence but have led to morbidity from mesh erosion, pain from collagen infiltration and scar plate formation along the route of the mesh, and difficulty with removal of the synthetic mesh when erosion occurs as a consequence of the tissue integration that occurs with these products.

A prior known approach to avoid the synthetic mesh is the use of biologic material, either autologous or heterologous. Unfortunately, the use of these biologic agents have not enjoyed high rates of success when used in pelvic surgery for incontinence or pelvic organ prolapse. Additionally, current delivery techniques use cystoscopy to confirm that an initial guidewire placement has not led to bladder, urethral, or vaginal injury. Once good placement of a smaller diameter guidewire is confirmed, placement of the larger sized sling along the tract of the guide is carried out. This approach can and does lead to unrecognized tissue injury to the bladder, urethra, or vagina. The shortcomings of current implantable slings and their delivery systems dictate the need to develop safer implants and delivery systems that are highly successful in the treatment of urinary incontinence.

Therefore a need thus exists for new devices and methods for the treatment of female urinary incontinence. A further need exists for new devices and methods comprising an implant that avoids the risks of the prior known suburethral mesh while maintaining the benefits of a minimally invasive technique. Additionally, a need exists for novel methods and devices that are able to ensure that no tissue damage occurs during the placement of the implanted devices.

SUMMARY

The disadvantages and deficiencies of the prior known approaches are addressed and overcome by the methods and apparatus embodiments provided herein. In the various embodiments, novel devices and methods for the treatment of urinary incontinence are provided. In various ones of the embodiments, an implantable suburethral suture sling comprised of two components and a delivery system is provided. The first component of the sling is a portion preferably made up of non-biodegradable sutures. In an example method embodiment, the sutures are implanted suburethrally. In an alternative embodiment, the sutures may be incorporated into a biodegradable matrix. The second component is an anchoring portion comprised of a non-biodegradable anchoring system that is positioned substantially away from the urethra. The anchoring system may be comprised of non-biodegradable mesh and/or a non-biodegradable anchors or anchoring system. In an alternative embodiment, slings may be placed on either side of or lateral to the urethra. In this embodiment, the sling components may be the same as for suburethral placement.

In an example embodiment, a device for treating urinary incontinence includes a plurality of non-biodegradable sutures configured in parallel and forming an implantable sling; and first and second non-biodegradable anchor portions coupled to opposing ends of the implantable sling.

In another example embodiment, a system for treating urinary incontinence includes a surgical delivery apparatus comprising a handle, a hollow shaft, and a removable tip; and an implantable sling positioned within the hollow shaft and further comprising a central portion configured for placement adjacent a portion of a urethra and first and second anchor portions attached at opposing ends of the central portion, wherein the central portion of the implantable sling further comprises a plurality of non-biodegradable sutures arranged in parallel.

In another example embodiment, a method for treating urinary incontinence includes providing at least one implantable sling comprising a plurality of non-biodegradable sutures configured in a generally parallel arrangement and further comprising anchor portions comprising non-biodegradable material attached to opposing ends of the plurality of non-biodegradable sutures; inserting at least one implantable sling into a human abdomen and positioning the plurality of non-biodegradable sutures adjacent a portion of a urethra; and positioning the anchor portions in tissue in the human abdomen a distance away from the urethra.

Recognition is made in the embodiments of the present application that the use of non-biodegradable suture material to form an implantable sling can reduce or eliminate urinary incontinence while advantageously avoiding the complications and disadvantages of the prior known solutions.

DETAILED DESCRIPTION

The illustrative examples described herein are presented for explanation purposes and are not to be read as limiting the scope of the present application, or to limit the scope of the appended claims. Various obvious alternatives can be used with the embodiments and these alternatives are contemplated by the inventor as forming additional alternative embodiments which are also within the scope of the appended claims.

Figure 1:
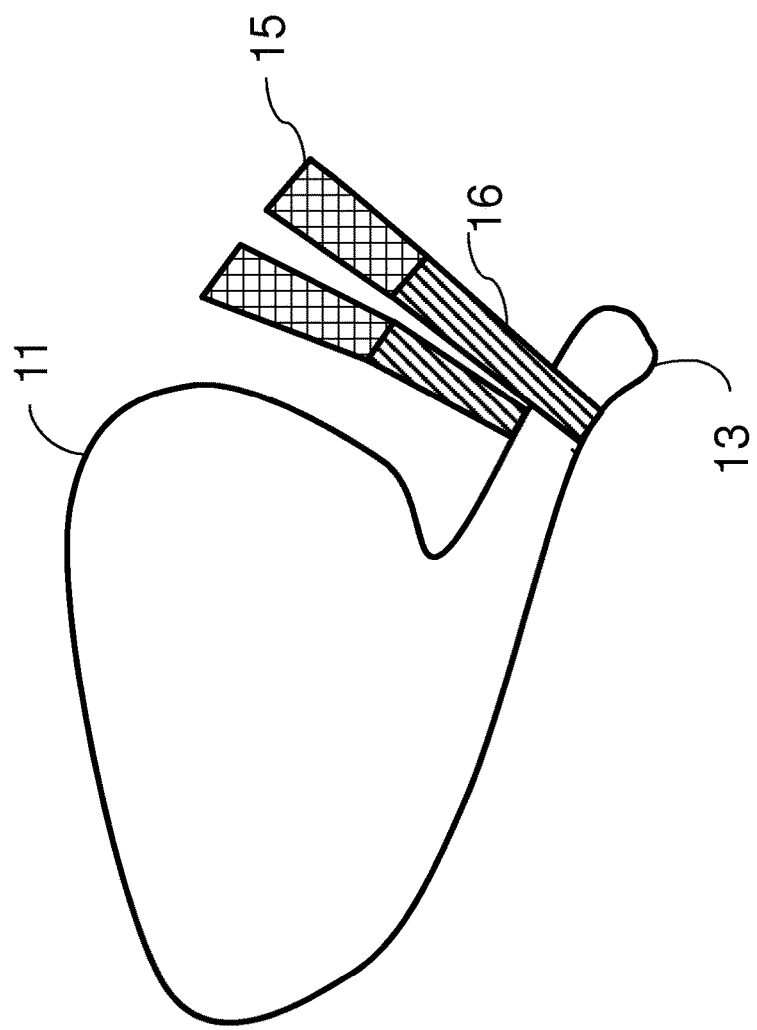
FIG. 1 illustrates in a lateral view one example embodiment device with a sling comprising sutures positioned under the urethra and anchors to support the sling.

FIG. 1 illustrates in a lateral view 10 one example embodiment device with a sling comprising sutures 16 and anchors 15 positioned proximal to a urethra 13 which extends from a female bladder 11. In the embodiment shown in FIG. 1, the example embodiment implantable device utilizes parallel non-biodegradable sutures 16 placed proximal to and under the urethra 13 or bladder neck, forming a "suburethral implant."

In some alternative embodiments, the implant sutures such as 16 in FIG. 1 may be comprised of any permanent suture. For example, the permanent sutures can be prolene. Alternative materials include, for example, polypropylene, polyamide, and polyethylene. The sling formed from the non-biodegradable sutures can be provided in a variety of sizes. In selected embodiments, the overall width of the sling or implant may range between about 0.5 and 2.5 centimeters. The non-biodegradable sutures are formed generally in parallel, although alignment between the sutures is not required, and spaced apart. In certain embodiments, the individual sutures can be spaced apart from one another by between about 0.5 to about 2.0 millimeters. In various embodiments, the width of the sling and spacing between sutures may be smaller or larger according to individual tissue and individual anatomy differences, or to accommodate different manufacturing preferences.

In addition, the various embodiments can include suture materials of different shapes. The cross section of the sutures comprising may be any shape. In example embodiments, the cross-sectional shape of the suture material can be oval or round. The stabilization and spacing of these sutures can be accomplished by the integration with a biodegradable or absorbable synthetic or non-synthetic support material. The support material can include biologic material such as human cadaver, animal fascia, or dura. Additionally, in various alternative embodiments, the support material can include absorbable material such as polyglactin mesh or the sutures can be coated with extracellular matrix hydrogel coating. In other alternative embodiments, the sutures could be free or unincorporated in a matrix.

Although scar formation around the urethral sutures will occur after the sling device is implanted, and the scar formation will operate to minimize any movement of the implanted sling, an anchoring system distant from the urethra is advantageous to further stabilize the urethral support and to avoid changes in the tensioning of the urethral sutures over time. As shown in FIG. 1, this anchoring can be accomplished by the use of synthetic mesh 15 placed away from the urethra 13. In the arrangement of FIG. 1, synthetic mesh is shown as the anchor material 15. If synthetic mesh is used, the permanent sutures 16 can be interwoven with the mesh 15. As described below, the anchor function can also be provided using alternative materials and methods.

Figure 2:
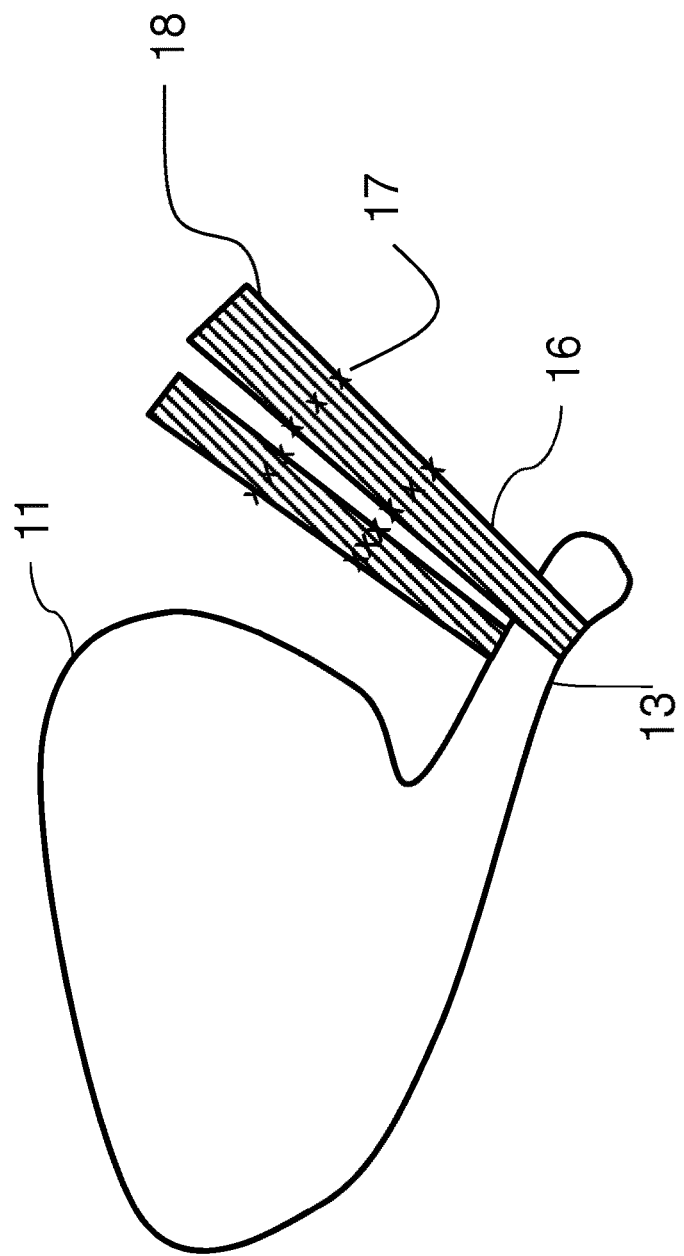
FIG. 2 illustrates in another lateral view another example embodiment of a sling device with sutures positioned under the urethra and having tined anchors to support the sling sutures.

FIG. 2 illustrates in a lateral view 30 an additional example embodiment device with an implantable sling comprising sutures 16 and anchors 18 positioned proximal to a urethra 13 which extends from a female bladder 11. In the embodiment shown in FIG. 2, the example implantable device again utilizes generally parallel non-biodegradable sutures 16 placed proximal to and under the urethra 13 or bladder neck, a suburethral implant.

In the alternative embodiment 30 of FIG. 2, the anchors 18 can be implemented using tines or barbs 17 placed along the sling away from the urethra 13. Alternatively, if tined or barbed anchors were used 90 they may be spaced along each individual suture ensuring that placement was away from the urethra and vagina. By keeping the anchor portions of the implantable sling device away from the urethra and vagina, complications that arise in the prior known approaches can be reduced or avoided when using the novel methods and the novel sling devices of the present application.

Figure 3:
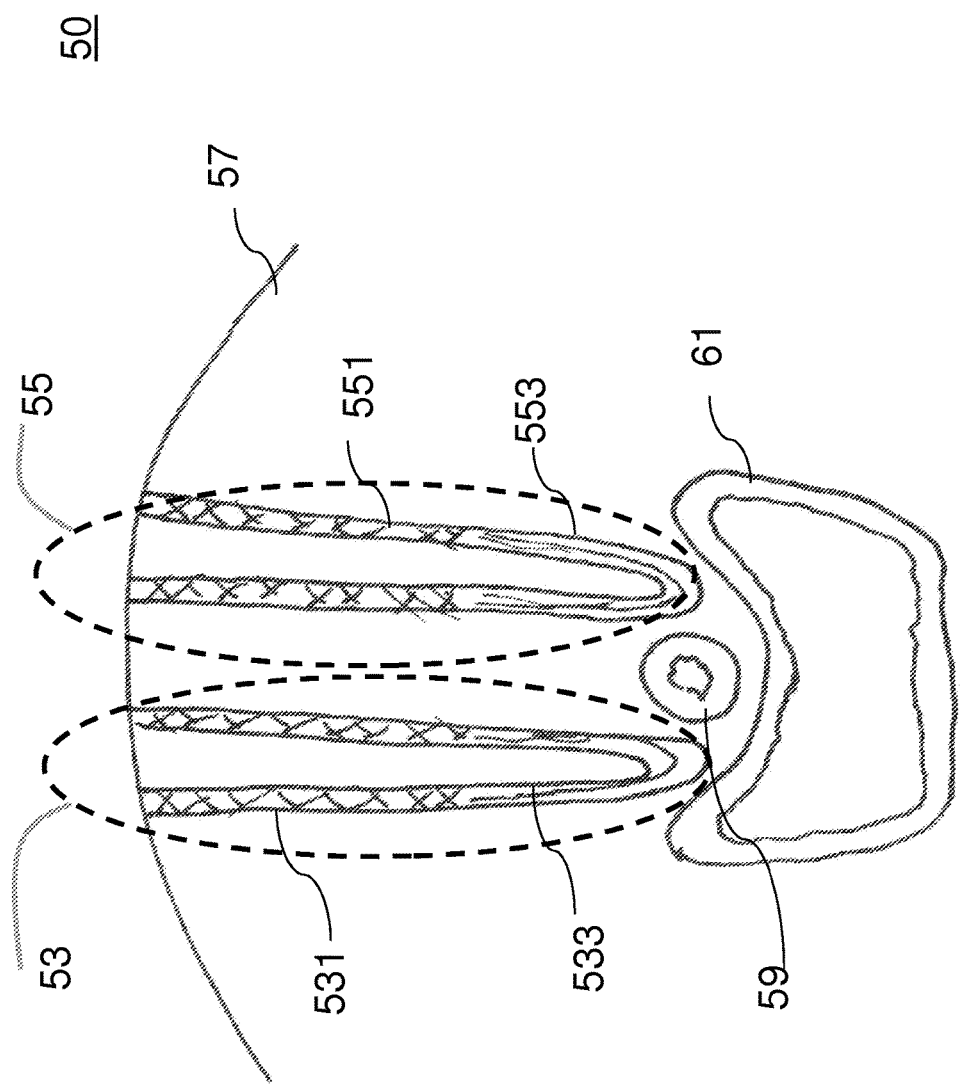
FIG. 3 illustrates in a cross sectional view an alternative embodiment device with a sling comprises of sutures positioned lateral to the urethra, on two opposing sides, and each sling comprising anchors positioned away from the urethra to support the sutures.

FIG. 3 illustrates, in a cross sectional view 50, an alternative embodiment using a pair of implantable devices 53, 55 each with a sling comprising sutures are positioned laterally with respect to the urethra 59, on two opposing sides. In this alternative embodiment, one implantable sling device may be placed on either side of the urethra, forming a "periurethral implant." In this alternative embodiment, the use of a periurethral implant approach can be performed by placing two implants of the slings comprising non-biodegradable suture material.

FIG. 3 illustrates the use of a first implantable sling 53 positioned on one side of a urethra 59, and a second implantable sling 55 positioned on an opposing side, contralaterally from the first implantable sling 53. Each of the implantable slings further comprises a plurality of generally parallel non-biodegradable sutures 533, and 553 respectively in FIG. 3, and each of the implantable slings 53, 55 further comprises anchor portions, 531 and 551 respectively, positioned away from the urethra 59 and the vagina 61 so that in this alternative embodiment, the sutures 533, 553 do not extend to a suburethral position but instead are positioned periurethrally. This arrangement has the advantage that no portion of the slings is positioned between the urethra 59 and the vagina 61, so that certain complications of the prior known approaches, including that the synthetic mesh of the prior slings can extend into the urethra, are avoided by use of the novel methods and apparatus of the present application.

In FIG. 3, the anchors 531, 551 of the slings 53, 55 are shown extending away from the sutures and ending proximal to the surface of the human abdomen, 57. During implantation the implants can be extended through incisions in the human abdomen and then cut to remove excess material with the anchors being positioned beneath the skin of the human abdomen; tension can be applied during the implantation surgery and maintained by the anchors 531, 551.

Figure 4:
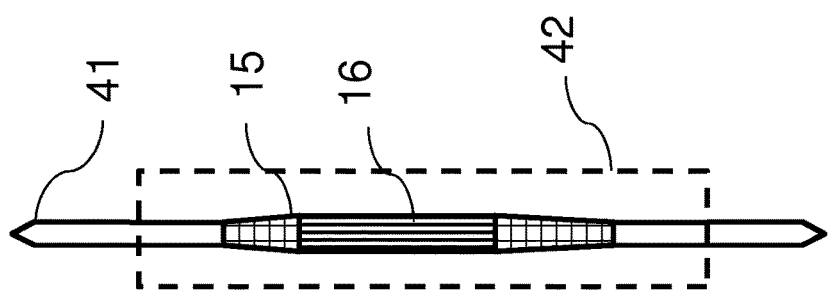
FIG. 4 illustrates in a plan view an example embodiment implantable sling device with sutures having anchors with mesh support.

FIG. 4 illustrates in a plan view an example embodiment implantable sling device 70 with sutures 16 having anchors 15 with mesh support, similar to the device shown in FIG. 1. As described above, the implantable sling can include sutures formed of non-biodegradable material including prolene, polypropylene, polyamide, and polyethylene, for example. The sutures can form a sling that can be of various widths, and may range between about 0.5 and 2.5 centimeters. The non-biodegradable sutures are formed generally in parallel, although alignment between the sutures is not required, and spaced apart. In certain embodiments, the individual sutures can be spaced apart from one another by between about 0.5 to about 2.0 millimeters. In various embodiments, the width of the sling and spacing between sutures may be smaller or larger according to individual tissue and individual anatomy differences, or to accommodate different manufacturing preferences.

FIG. 4 depicts an arrangement where the ends of the sling device may be affixed to a tapered plastic tube or needle 41 to allow passage through a delivery system (described below). In various embodiments, the implant may or may not be covered with a removable sheath 42 for use in implanting the device 70.

Figure 5:
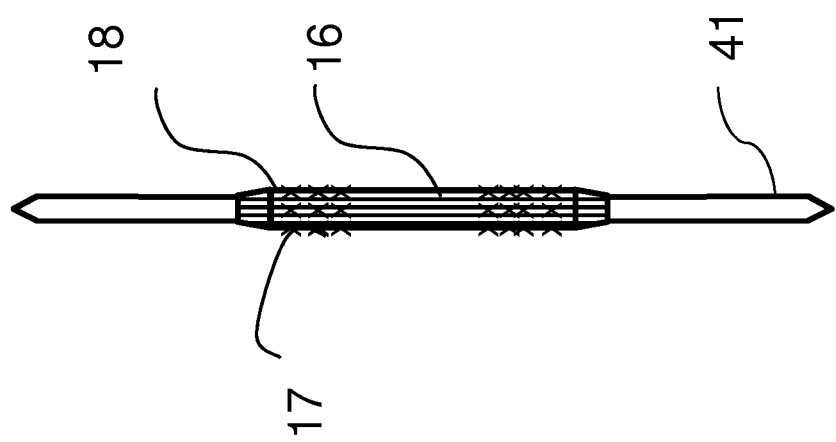
FIG. 5 illustrates in a plan view an alternative embodiment implantable sling device with tined anchor supports.

FIG. 5 illustrates in a plan view an alternative embodiment implantable sling device 90 with tined anchor supports. In FIG. 5, the non-biodegradable sutures 16 are again arranged generally in parallel and spaced apart to form a sling having a desired width as described above. In this embodiment, which is similar to that illustrated in FIG. 2 above, tines or barbs 17 are used along the suture material to form anchor portions 18.

In FIG. 5, an arrangement is depicted where the ends of the sling device 90 can be affixed to a tapered plastic tube or needle 41 to allow passage through a delivery system (described below). In various embodiments, the implant may or may not be covered with a removable sheath for use in implanting the device 90.

Figure 6:
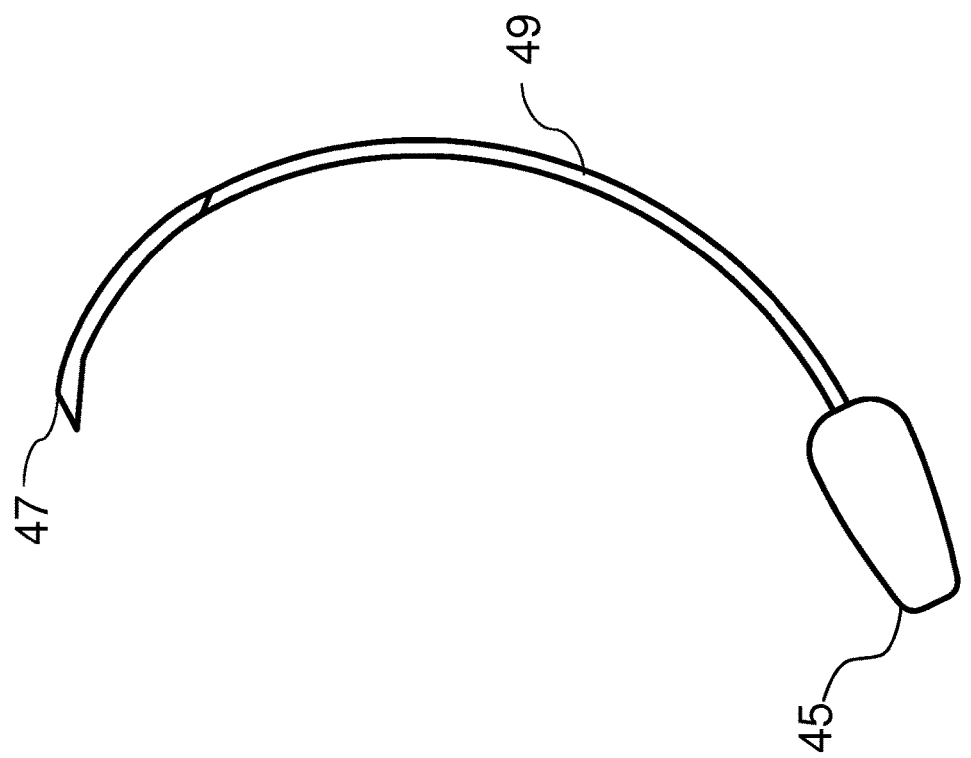
FIG. 6 illustrates in a side view an example embodiment of a surgical delivery device for use with the various implantable sling embodiments described herein.

FIG. 6 illustrates in a side view an example embodiment of a surgical delivery device 110, which is referred to herein as a trocar, for use with the various implantable sling embodiments described herein. The trocar 110 for sling placement can be comprised of three portions or sections 45, 49, and 47. The illustrative example embodiment trocar 110 includes a handle 45, a hollow shaft 49 through which the implant can be placed, and a tip 47, that can be fixed or be removable. In some alternative embodiments, the delivery system 110 can be reusable to decrease medical cost and reduce medical waste.

In additional method embodiments, the implantable sling devices can be placed using the trocar 110 by making one incision of approximately 1-5 cm longitudinal length along the suburethral portion of the anterior vaginal wall. Dissection of the vaginal mucosa can be carried out laterally. One or more incisions can be made superior or inferior to the pubic bone on the patient's abdomen and these incisions can be placed lateral to the midline. The exact location of the abdominal incision(s) and vaginal incision(s) can be varied to suit surgeon preference and to meet the patient's individual needs. The delivery device or trocar 110 can then be passed through the abdomen in one of several ways. In some embodiments, one technique is to insert the tip 47 beginning from the incision in the vagina and then pass the tip through to the abdominal incision in a "bottom up approach." In other embodiments, another technique can pass the trocar from the abdominal incision to the vaginal incision in a "top down approach."

In additional method embodiments that are also contemplated by the inventor as forming alternative embodiments herein, one or more additional trocars may be used to pass through the patient's abdomen on the contralateral side. During passage of the trocar a catheter containing a stylet can be used to allow deflection of the urethra to minimize risk of urethral injury during placement of one or more of the implantable sling devices of the embodiments.

The various methods embodiments using the surgical delivery system allows the surgeon to choose the approach for trocar passage and to choose a different technique for each side if desired. For example, the trocar can be passed from the bottom up on the patient's right side and then top down on the patient's left side. Cystoscopy can be performed after placing one or more trocars to enable the surgeon to ensure no injury has occurred to the bladder, urethra, or other tissues. Inspection of the vagina can also be performed to ensure that no damage or perforation of the vagina has occurred.

In additional method embodiments, after confirmation that no injury has occurred, the tips of the trocar(s) can be removed and the plastic ends of the implant device or devices can be passed through the hollow trocars. Once the ends of the implantable device are passed, the trocars may be removed as the sutures underlying or adjacent to the urethra are tensioned to the surgeon's preference. In an additional method embodiment, following the placement of the implantable device(s), the implant may be cut flush with the skin on the patient's abdomen. In an additional embodiment, the skin of the patient's abdominal wall can be elevated to allow the device to fall below the skin surface. Preferably, the skin may be then sutured closed with absorbable suture. In an example where an incision in the vagina wall beneath the urethra was made, the suburethral incision may also be closed with one or more absorbable sutures.

In various alternative method embodiments, when using either a suburethral or periurethral implant position of the implantable device(s), the trocar tip could be a portion of the anchoring system. In a variation of the method embodiments, using such a system allows implant placement through a single vaginal incision. The implantable device can be attached to the trocar tip and placed, at least partially, within the hollow trocar shaft. The trocar could be designed to allow an opening along the length of the shaft to remove the implant. The handle/trocar interface could be designed to allow a portion of the sling not being placed to be exterior to the handle or trocar. In this embodiment, after confirming placement without adjacent tissue injury, withdrawal of the trocar would leave the implant in place. A stylet may be used to provide countertraction during trocar removal.

In still other alternative embodiments, alternative placement options can be used for implant placement. These additional embodiment method options can include a transobturator approach for passage of the trocar to allow implant placement. Such an approach can be accomplished in either an "outside in" or an "inside out" approach. In an embodiment using the "outside in" approach, the trocar is inserted by making an incision on the lateral edge of the labia majora and passing the trocar into the vaginal incision. In an additional alternative method, this placement can also be accomplished by an "inside out" approach by passing the trocar from the vaginal incision to a skin incision made near the labia majora. In still other method embodiments, placement of the implant could include placement in front of the pubic bone "prepubic" rather than "retropubic" placement or in combination of prepubic and retropubic placement.

In additional method embodiments that are also contemplated by the inventor as providing additional aspects of the present application, various modifications to the general trocar design 110 shown in FIG. 6 can be used to enable alternative methods of implant placement.

As described above, use of the various embodiments of the present application provides implantable sling devices and methods that can reduce or eliminate urinary incontinence while yet overcoming the disadvantages and deficiencies of the prior known solutions.

Although the example illustrative embodiments have been described above in detail, it should be understood that various changes, substitutions and alterations can be made herein without departing from the spirit and scope of the present application as defined by the appended claims.

Moreover, the scope of the present application is not intended to be limited to the particular illustrative example embodiments of the process, machine, manufacture, and composition of matter means, methods and steps described in this specification. As one of ordinary skill in the art will readily appreciate from the disclosure, processes, machines, manufacture, compositions of matter, means, methods or steps, presently existing or later to be developed, that perform substantially the same function or achieve substantially the same result as the corresponding example arrangements described herein may be utilized according to the illustrative embodiments presented and alternative arrangements described, suggested or disclosed. Accordingly, the appended claims are intended to include within their scope such processes, machines, manufacture, compositions of matter, means, methods, or steps.

What is claimed is:

1. A device for treating urinary incontinence, comprising:
a plurality of non-biodegradable sutures configured generally in parallel and forming an implantable sling free from biologic material, the plurality of non-biodegradable sutures integrated with a non-biologic support material, and the non-biodegradable sutures free from intersections with one another, free from barbs and free from tines, and free from junctures with any fiber and free from junctures with any woven material along a length of the implantable sling; and
first and second non-biodegradable anchor portions coupled to opposing ends of the implantable sling.

2. The device of claim 1, wherein the plurality of non-biodegradable sutures further comprises polypropylene.

3. The device of claim 1, wherein the plurality of non-biodegradable sutures further comprises a material that is one chosen from the group consisting essentially of polypropylene, polyamide, and polyethylene.

4. The device of claim 1, wherein the plurality of non-biodegradable sutures are spaced from one another by a distance between about 0.5 to 2.0 millimeters.

5. The device of claim 1, wherein the implantable sling formed by the non-biodegradable sutures has a width between about 0.5 and 2.5 centimeters.

6. The device of claim 1, wherein the plurality of non-biodegradable sutures is integrated with the non-biologic support material that is a matrix of biodegradable material.

7. The device of claim 6 wherein the biodegradable material is one chosen from the group consisting essentially of absorbable synthetic material and polyglactin mesh.

8. The device of claim 1, wherein the first and second anchor portions further comprise a non-biodegradable mesh.

9. The device of claim 1, wherein the first and second anchor portions further comprise anchors that are one selected from tines and barbs placed along the sutures that form the implantable sling.

10. The device of claim 9, and further comprising a removable sheath covering the implantable sling.

11. A system for treating urinary incontinence, comprising:
a surgical delivery apparatus comprising a handle, a hollow shaft, and a removable tip; and
an implantable sling free from biologic material disposed within the hollow shaft and further comprising a central portion configured for placement adjacent a portion of a urethra and first and second anchor portions attached at opposing ends of the central portion, wherein the central portion of the implantable sling further comprises a plurality of non-biodegradable sutures arranged in parallel, the plurality of non-biodegradable sutures integrated with a non-biologic support material, and the non-biodegradable sutures free from intersections with one another, free from barbs and free from tines, and free from junctures with any fiber and free from junctures with any woven material along a length of the implantable sling.

12. The system of claim 11, wherein the central portion of the implantable sling further comprises a biodegradable matrix material positioned around the plurality of non-biodegradable sutures.

13. The system of claim 11, wherein the plurality of non-biodegradable sutures within the implantable sling further comprise a material that is one selected from the group consisting essentially of polypropylene, polyamide, and polyethylene.

14. The system of claim 11, wherein the first and second anchor portions further comprise a non-biodegradable mesh.

15. The system of claim 11 and further comprising a removable sheath apparatus covering the implantable sling.

16. A method for treating urinary incontinence, comprising:
providing at least one implantable sling free from biologic material comprising a plurality of non-biodegradable sutures configured in a generally parallel arrangement and further comprising anchor portions comprising non-biodegradable material attached to opposing ends of the plurality of non-biodegradable sutures, the plurality of non-biodegradable sutures integrated with a non-biologic support material, and the non-biodegradable sutures free from intersections with one another, free from barbs and free from tines, and free from junctures with any fiber and free from junctures with any woven material along a length of the implantable sling;
inserting the at least one implantable sling into a human abdomen and positioning the plurality of non-biodegradable sutures adjacent a portion of a urethra; and
positioning the anchor portions in tissue in the human abdomen a distance away from the urethra.

17. The method of claim 16, wherein inserting the at least one implantable sling further comprises positioning the plurality of non-biodegradable sutures configured in a parallel arrangement suburethrally.

18. The method of claim 16, wherein inserting the at least one implantable sling further comprises:
placing the at least one implantable sling adjacent one side of the urethra so that the plurality of non-biodegradable sutures are disposed periurethrally; and
inserting a second implantable sling into the human abdomen and positioning a second plurality of non-biodegradable sutures arranged in parallel adjacent another side of the urethra opposite to the at least one implantable sling so that the plurality of non-biodegradable sutures for the second implantable sling are also disposed periurethrally.

19. The method of claim 16, wherein the step of inserting the at least one implantable sling further comprises providing a surgical delivery device comprising a handle, a hollow shaft containing the at least one implantable sling, and a removable tip that is inserted into the human abdomen.

20. The method of claim 19, and further comprising inserting the tip of the surgical delivery device into an incision made in a suburethral portion of a human vagina and passing the tip and the hollow shaft through the tissue of the human abdomen to an incision made in the human abdomen; removing the tip of the surgical delivery device, placing the anchors at one end of the implantable sling in tissue of the human abdomen; and subsequently removing the surgical delivery device leaving the implantable sling with the plurality of non-biodegradable sutures positioned suburethrally.

* * * * *